United States Patent
Yamada et al.

(10) Patent No.: US 11,519,901 B2
(45) Date of Patent: Dec. 6, 2022

(54) METHOD FOR SCREENING FOR CANCER THERAPEUTIC AGENT

(71) Applicant: THE UNIVERSITY OF TOKYO, Tokyo (JP)

(72) Inventors: Yasuhiro Yamada, Kyoto (JP); Katsunori Semi, Kyoto (JP); Knut Woltjen, Kyoto (JP); Yutaka Matsuda, Kamakura (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/563,987

(22) PCT Filed: Apr. 1, 2016

(86) PCT No.: PCT/JP2016/060974
§ 371 (c)(1),
(2) Date: Oct. 3, 2017

(87) PCT Pub. No.: WO2016/159376
PCT Pub. Date: Oct. 6, 2016

(65) Prior Publication Data
US 2018/0136195 A1    May 17, 2018

(30) Foreign Application Priority Data

Apr. 3, 2015 (JP) .............. JP2015-077264

(51) Int. Cl.
*C12Q 1/68* (2018.01)
*G01N 33/50* (2006.01)
*C12Q 1/6886* (2018.01)

(52) U.S. Cl.
CPC ....... *G01N 33/5011* (2013.01); *C12Q 1/6886* (2013.01); *G01N 2333/495* (2013.01); *G01N 2333/82* (2013.01); *G01N 2500/04* (2013.01); *G01N 2500/10* (2013.01)

(58) Field of Classification Search
None
See application file for complete search history.

(56) References Cited

U.S. PATENT DOCUMENTS

2013/0065887 A1    3/2013    Bhatia et al.

FOREIGN PATENT DOCUMENTS

WO    WO 2013/126993 A1    9/2013

OTHER PUBLICATIONS

Gu et al (Cancer Letters, 2014, vol. 343, pp. 200-209).*
Miyoshi et al (PNAS, 2010, vol. 107, No. 1, pp. 40-45).*
Hiti et al. (Molecular and Cellular Biology, 1989, vol. 9, No. 11, pp. 4722-4730).*
Nagai et al Biochemical and Biophysical Research Communications, 2010, vol. 395, pp. 258-263.*
Kosaka et al., "Identification of drug candidate against prostate cancer from the aspect of somatic cell reprogramming," *Cancer Sci.*, 104(8): 1017-1026 (2013).
Matsuda et al., "Application of iPS cell technology to cancer epigenome study: Uncovering the mechanism of cell status conversion fordrug resistance in tumor," *Pathol. Int.*, 64(7): 299-308 (2014).
Semi et al., "Application of somatic cell programming in cancer epigenetics research," *Experimental Medicine*, 32(19): 3061-3065 (2014).
Japanese Patent Office, International Search Report in International Patent Application No. PCT/JP2016/060974 (dated Jun. 28, 2016).
Takahashi, "Cellular reprograming—lowering gravity on Waddinton's epigenetic landscape," *Journal of Cell Science*, 125(11): 2553-2560 (2012).

* cited by examiner

*Primary Examiner* — Celine X Qian
(74) *Attorney, Agent, or Firm* — Leydig, Voit & Mayer, Ltd.

(57) ABSTRACT

The invention aims to provide a method of screening for a therapeutic drug for cancer as a molecular-targeted drug targeting some protein from a number of candidate target proteins, without identifying the true target protein. In particular, the invention provides a method of screening for a therapeutic drug for cancer, including (i) a step of expressing an exogenous cell regulatory factor in a target cancer cell under contact or no contact with a test substance, (ii) a step of confirming change in the cancer cell, and (iii) a step of selecting the test substance as a therapeutic drug for cancer when the change of cancer cell increased under contact with the test substance as compared to no contact therewith.

1 Claim, 10 Drawing Sheets

A

B

A

B

A

B

Targeting vector h*NANOG* locus

METHOD FOR SCREENING FOR CANCER THERAPEUTIC AGENT

CROSS-REFERENCE TO RELATED APPLICATIONS

This patent application is the U.S. national phase of International Patent Application No. PCT/JP2016/060974, filed Apr. 1, 2016, which claims the benefit of Japanese Patent Application No. 2015-077264, filed on Apr. 3, 2015, which are incorporated by reference in their entireties herein.

TECHNICAL FIELD

The present invention relates to a method of screening for a therapeutic drug for cancer.

BACKGROUND ART

In a cancer treatment in recent years, many cases show that a molecular-targeted drug, that is, a therapeutic drug directly targeting a protein related to an important intracellular signal involved in the proliferation or progress of cancer cells, is effective, and searches for a protein that can be a novel drug discovery target have been actively performed. As a target candidate protein for cancer therapy, proteins encoded by genes peculiarly or excessively expressed in cancer cells are exemplified. While many genes encoding such target candidate proteins can be found by comprehensive analyses such as microarray method, identification of a true target gene encoding a protein that can actually be a target of cancer treatment among them requires excessive experimentation.

In addition, a technique for reprogramming somatic cells has been developed and attempts have been made to reprogram cancer cells (non-patent document 1). However, such attempts mainly focus on changing the properties of cancer cells themselves, and there is no report on screening for a therapeutic drug for cancer by utilizing reprogramming of cancer cells.

DOCUMENT LIST

Non-Patent Document non-patent document 1: Kosaka T, et al, Cancer Sci. 104: 1017-1026, 2013

SUMMARY OF THE INVENTION

Problems to be Solved by the Invention

The problem of the present invention is provision of a method for screening for a therapeutic drug for cancer.

Means of Solving the Problems

The present inventors have conducted intensive studies in an attempt to solve the aforementioned problems and found that reprogramming or differentiation is enhanced by suppressing expression of known target genes (i.e., genes encoding proteins known to be related to important intracellular signals involved in proliferation or progression of cancer cells) when the cancer cell is reprogrammed or directly induced to differentiate into another cell type; in other words, they have found that proteins encoded by these target genes have a function to maintain characteristics as cancer cells and suppress change of the fate of cancer cells. Furthermore, the inventors introduced reprogramming factors into cancer cells expressing target proteins for existing molecular-targeted drugs under contact with the molecular-targeted drugs and confirmed that the degree of reprogramming was enhanced as compared to reprogramming under no contact with drugs. Therefore, it was clarified that when a cancer cell, for which an effective target protein is known, is, under contact with a test substance, reprogrammed or directly induced to differentiate into a different cell type and the reprogramming or differentiation is promoted, the test substance can be confirmed to have a function to suppress activity of the target gene. Even when any cancer cell is targeted, once the test substance promotes reprogramming or differentiation of the cancer cell, the test substance can be assumed to have a function to suppress activity of some protein related to intracellular signals involved in the proliferation or progression of the cancer cell. Therefore, it is possible to directly screen for a candidate substance of a therapeutic drug for cancer, without identifying the target protein (target gene).

The present inventors have conducted further studies based on these findings and completed the present invention.

That is, the present invention provides the following method.

[1] A method of screening for a therapeutic drug for cancer, comprising the following steps;
(i) a step of expressing an exogeneous cell regulatory factor in a target cancer cell under contact or no contact with a test substance,
(ii) a step of confirming change in the cancer cell, and
(iii) a step of selecting the test substance as a therapeutic drug for cancer when the change of cancer cell increased under contact with the test substance as compared to no contact therewith.
[2] The method of [1], wherein the aforementioned cell regulatory factor is a reprogramming factor, and the aforementioned change in the cancer cell is reprogramming of the cancer cell.
[3] The method of [2], wherein the aforementioned reprogramming factor comprises Oct3/4, Sox2, Klf4 and c-Myc.
[4] The method of [2] or [3], wherein the aforementioned reprogramming of the cancer cell is evaluated using the number of cells positive for an undifferentiation-specific antigen, or an expression level of an undifferentiation-specific gene in the cancer cell as an index.
[5] The method of [4], wherein the aforementioned undifferentiation-specific gene is one or more genes selected from Nanog, Epcam, Cdh1, Fbxo15, PODXL and GDF3.
[6] The method of [2] or [3], wherein the aforementioned reprogramming of the cancer cell is evaluated using the number of formed colonies as an index.
[7] The method of [1], wherein the aforementioned cell regulatory factor is MyoD1, and the aforementioned change of the cancer cell is change from the cancer cell to a myotube cell.
[8] The method of [7], wherein the aforementioned change from the cancer cell to the myotube cell is evaluated using an expression level of myogenin or myosin heavy chain as an index.
[9] A method of identifying a protein capable of becoming a drug discovery target of a therapeutic drug for cancer, comprising the following steps:
(i) a step of expressing an exogeneous cell regulatory factor in a cancer cell comprising a gene encoding a test protein in an expression regulatable form, under conditions resulting in the expression of the gene or under conditions suppressing expression of the gene, (ii) a step of confirming change in the cancer cell, and (iii) a step of selecting the test protein as a protein capable of becoming a drug discovery target of a therapeutic drug for cancer, when the change of the cancer cell increased under conditions suppressing expression of the gene, as compared to that under conditions resulting in the expression of the gene.

Effect of the Invention

According to the present invention, identification of the target gene is not necessary, and a therapeutic drug for cancer to be a molecular-targeted drug can be directly screened for. In addition, the present invention enables screening for a therapeutic drug for cancer which shows a high effect on cancer cells.

DESCRIPTION OF EMBODIMENTS

Figure 1:
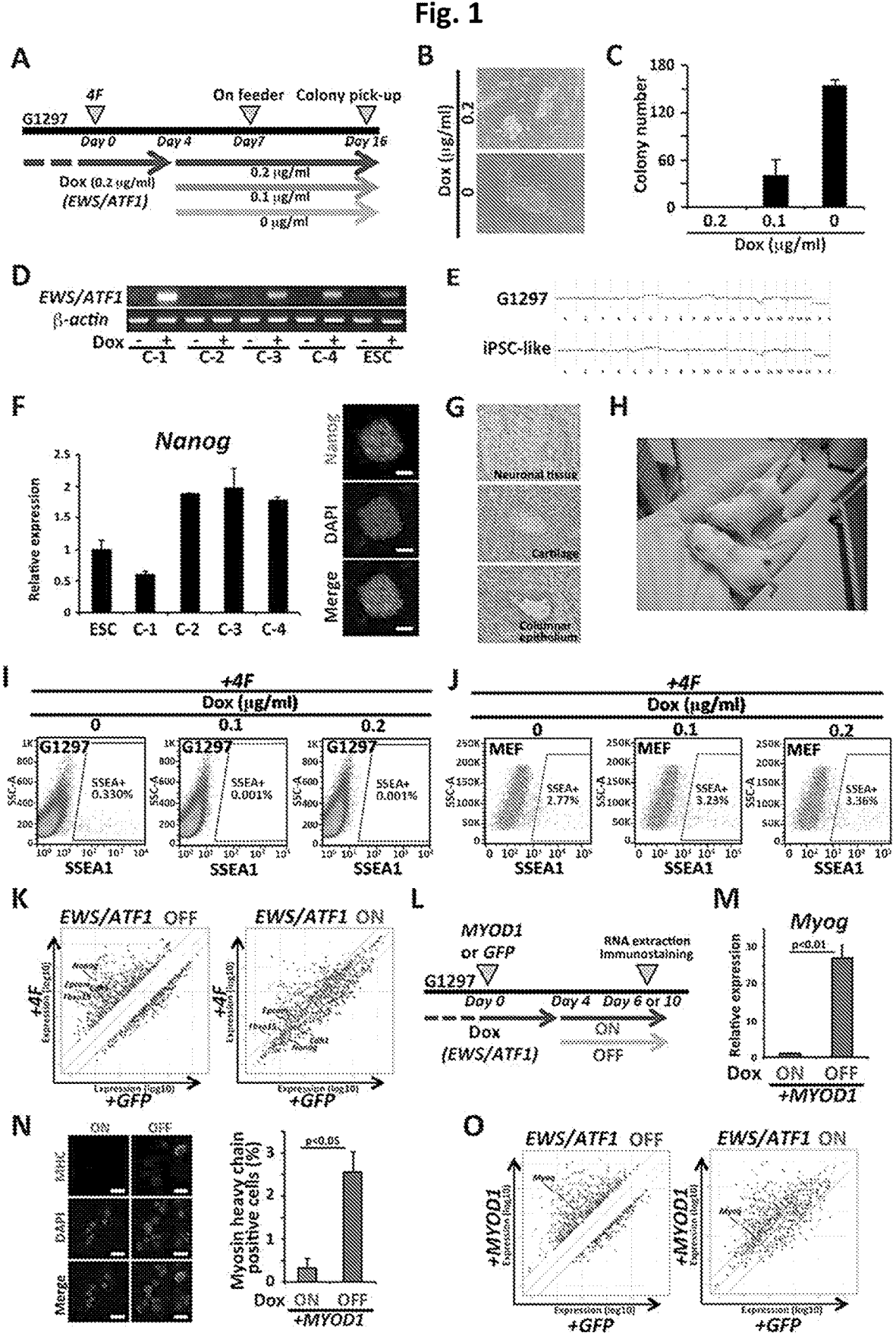
FIG. 1A is a schematic drawing describing induction of EWS/ATF1 expression and a method of introducing a reprogramming factor.
FIG. 1B shows a phase contrast microscopic image of sarcoma cell line G1297 after introduction of a reprogramming factor, when the expression of EWS/ATF1 was induced (DOX 0.2 μg/ml) or was not induced (DOX 0 μg/ml).
FIG. 1C shows the measurement results of the number of colonies formed after introduction of a reprogramming factor, when the expression of EWS/ATF1 was induced (DOX 0.2 or 0.1 μg/ml) or was not induced (DOX 0 μg/ml).
FIG. 1D shows the results of induction of EWS/ATF1 expression into iPS cell lines (C-1, C-2, C-3 and C-4), established from sarcoma cell line G1297, by the addition of 0.2 μg/ml DOX as confirmed by RT-PCR.
FIG. 1E shows the results of chromosomal microarray (CGH array) analysis of sarcoma cell line G1297 and iPS cell lines established from the cell line G1297.
FIG. 1F shows the measurement results of the expression of Nanog in iPS cell lines (C-1, C-2, C-3 and C-4) by RT-PCR (left Figure) and stained image of iPS cell line stained with Nanog and DAPI (right Figure).
FIG. 1G shows stained images of teratoma formed by subcutaneously transplanting iPS cell established from sarcoma cell line G1297 to nude mouse.
FIG. 1H is a photograph of chimeric mice developed by injecting iPS cell established from sarcoma cell line G1297 into blastocyst.
FIG. 1I shows the results of FACS measuring the positive rate of SSEA1 on day 10 of introduction of a reprogramming factor (4F) into sarcoma cell line G1297, when the expression of EWS/ATF1 was induced (DOX 0.2 or 0.1 μg/ml) or was not induced (DOX 0 μg/ml) on day 4 of 4F introduction.
FIG. 1J shows the results of FACS measuring the positive rate of SSEA1 on day 10 of introduction of a reprogramming factor (4F) into mouse embryonic fibroblast (MEF), when the expression of EWS/ATF1 was induced (DOX 0.2 or 0.1 μg/ml) or was not induced (DOX 0 μg/ml) on day 4 of 4F introduction.
FIG. 1K shows the results of microarray analysis using RNA recovered from the cells on day 6 after introduction of a reprogramming factor (4F) or introduction of GFP into sarcoma cell line G1297, when the expression of EWS/ATF1 was induced (ON) or was not induced (OFF) on day 4 after 4F introduction or GFP introduction.
FIG. 1L is a schematic drawing describing a method of induction of EWS/ATF1 expression and introduction of MYOD1.
FIG. 1M shows the measurement results of the expression of Myogenin by RT-PCR, when the expression of EWS/ATF1 was induced (ON) or was not induced (OFF) in the cells of sarcoma cell line G1297 introduced with MYOD1.
FIG. 1N shows stained images when stained with Myosin heavy chain (MHC) and DAPI (left Figure) and the measurement results of the expression of Myosin heavy chain by RT-PCR (right Figure), when the expression of EWS/ATF1 was induced (ON) or was not induced (OFF) in the cells of sarcoma cell line G1297 introduced with MYOD1.
FIG. 1O shows the results of microarray analysis using RNA recovered from the cells on day 6 after introduction of MYOD1 or introduction of GFP into sarcoma cell line G1297, when the expression of EWS/ATF1 was induced (ON) or was not induced (OFF) on day 4 after MYOD1 introduction or GFP introduction.

The present invention provides a method of screening for a therapeutic drug for cancer, comprising the following steps;

(i) a step of expressing an exogenous cell regulatory factor in a target cancer cell under contact or no contact with a test substance,
(ii) a step of confirming change in the cancer cell, and
(iii) a step of selecting the test substance as a therapeutic drug for cancer when the change of cancer cell increased under contact with the test substance as compared to no contact therewith.

Cancer Cell

In the present invention, cancer means malignant tumor. It is not limited to particular cancer and includes carcinoma (malignant tumor derived from epithelial cell), sarcoma, other leukemia and the like. The cancer cell to be used in the present invention is a cell constituting malignant tumor, which may be an establish cell or a cell isolated from the body. In addition, the cancer cell to be used in the present invention may be a cancer cell for which an effective target protein is known (namely, known to be sensitive to a certain existing molecular-targeted drug) (e.g., EWS/ATF1 fusion gene forced expression cancer cell, gefitinib-sensitive mutated EGFR expression cancer cell, Lapatinib-sensitive HER2-amplified cancer cell, alectinib-sensitive EML4-ALK fusion gene expressing cancer cell, imatinib-sensitive chronic myeloid leukemia cell and the like), or a cancer cell for which an effective target protein is unknown.

The cancer cell to be used for the screening method of the present invention may contain a reporter gene. Examples of the reporter gene include, but are not limited to, luciferase gene, fluorescence protein gene, drug resistance gene and the like. Examples of the luciferase gene include fireflyluciferase gene, synthetic Renilla luciferase gene, secretory luciferase gene and the like, with preference given to secretory luciferase gene since proteins can be recovered easily. Examples of the fluorescence protein gene include green fluorescence protein genes such as GFP, EGFP and the like, blue fluorescence protein genes such as BFP, TagBFP and the like, red fluorescence protein genes such as RFP, DsRed and the like, and the like. Examples of the drug resistance gene include kanamycin resistance gene, ampicillin resistance gene, neomycin resistance gene, puromycin resistance gene, Blasticidin resistance gene and the like.

A reporter cell can be produced by, for example, knocking in a reporter gene to a particular gene locus in the genome by homologous recombination and the like. Homologous recombination may be performed using a genome editing technique. Examples of the genome editing technique include a method using zinc finger nuclease (ZFN) in which a zinc finger DNA-binding domain and a non-specific DNA cleavage domain are linked (JP-B-4968498), a method using TALEN (TAL effector nuclease) in which Transcription activator-like (TAL) effector, which is a DNA-binding module, and DNA endonuclease are linked (National Publication of International Patent Application No. 2013-513389), and a method utilizing CRISPR-Cas9 system in which DNA sequence CRISPR (Clustered Regularly interspaced short palindromic repeats) and nuclease Cas protein family having an important function along with CRISPR are combined (National Publication of International Patent Application No. 2010-519929). Examples of the particular gene locus include a gene locus which does not permit easy suppression of the expression of the inserted gene since it has an open chromatin structure such as human PPP1R2C gene locus and the like, and a gene locus of a gene specifically highly expressed in pluripotent cells (e.g., Nanog, Oct3/4, Fbx15 and the like, preferably Nanog). Examples of the recombinant cell containing such reporter gene include MEF derived from transgenic mouse incorporating green fluorescence protein (GFP) gene and puromycin resistance gene in the Nanog gene locus (Okita et al., Nature, 448, 313-317(2007)) and the like.

Cell Regulatory Factor

In the present invention, the cell regulatory factor is a factor that changes the properties of the cell by intracellular introduction and change the cell into other cell type. Examples thereof include, but are not particularly limited to, reprogramming factor, nerve cell inducer, neural stem cell inducer, neural crest cell inducer, myocardial cell inducer, muscle cell inducer, chondrocyte inducer, hepatocyte inducer, melanocyte inducer, hematopoietic progenitor cell inducer, erythroblast inducer and megakaryocyte progenitor cell inducer and the like.

Examples of the reprogramming factor to be used in the present invention include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, Glis1, GDF3 and the like, and gene products thereof. These reprogramming factors may be used alone or used in combination. Examples of the combination of reprogramming factors include the combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO 2010/056831, WO2010/068955, WO2010/098419, WO2010/102267, WO 2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat. Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat. Cell Biol. 11:197-203, R. L. Judson et al., (2009), Nat. Biotechnol., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, MaliP, et al. (2010), Stem Cells. 28:713-720, and Maekawa M, et al. (2011), Nature. 474:225-9. More preferable reprogramming factors are combinations containing Oct3/4, Sox2, Klf4 and c-Myc.

The above-mentioned reprogramming factors also include factors used for the purpose of enhancing establishment efficiency such as histone deacetylase (HDAC) inhibitor [for example, low molecular weight inhibitors such as valproic acid (VPA), trichostatin A, sodium butyrate, MC 1293, M344 and the like, nucleic acid-based expression inhibitor such as siRNA and shRNA against HDAC (e.g., HDAC1 siRNA Smartpool (registered trade mark) (Millipore), HuSH 29 mer shRNA Constructs against HDAC1 (OriGene) etc.) and the like, and the like], MEK inhibitor (e.g., PD184352, PD98059, U0126, SL327 and PD0325901), Glycogen synthase kinase-3 inhibitor (e.g., Bio and CHIR99021), DNA methyltransferase inhibitor (e.g., 5-azacytidine), histone methyltransferase inhibitor (e.g., low molecular weight inhibitor such as BIX-01294 and the like, nucleic acid-based expression inhibitor such as siRNA and shRNA against Suv39hl, Suv39h2, SetDB1 or G9a, and the like, and the like), L-channel calcium agonist (e.g., Bayk8644), butyric acid, TGFβ inhibitor or ALK5 inhibitor (e.g., LY364947, SB431542, 616453 and A-83-01), p53 inhibitor (e.g., siRNA and shRNA against p53), ARID3A inhibitor (e.g., siRNA and shRNA against ARID3A), miRNA such as miR-291-3p, miR-294, miR-295, mir-302 and the like, Wnt Signaling (e.g., soluble Wnt3a), neuropeputide Y, prostaglandins (e.g., prostaglandin E2 and prostaglandin J2), hTERT, SV40 LT, UTF1, IRX6, GLIS1, PITX2, DMRTB1 and the like. In the present specification, these factors used for improving the establishment efficiency are not especially distinguished from the reprogramming factor.

Examples of the nerve cell inducer to be used in the present invention include Lhx3, Ngn2 and Isl1 (WO2014/148646), Ascl1, Brn2 and Mytl1 (Wapinski O L et al, Cell. 155:621-635, 2013) and the like.

Examples of the neural stem cell inducer to be used in the present invention include Brn4/Pou3f4, Sox2, Klf4, c-Myc and E47/Tcf3 (Han D W et al, Cell Stem Cell. 10:465-472, 2012) and the like.

Examples of the neural crest cell inducer to be used in the present invention include SOX10 (Kim Y J, et al, Cell Stem Cell. 15:497-506, 2014) and the like.

Examples of the myocardial cell inducer to be used in the present invention include Gata4, Mef2c and Tbx5 (Ieda M et al, Cell. 142:375-386, 2010) and the like.

Examples of the muscle cell inducer to be used in the present invention include MYOD1, MYF5 (Tanaka A, et al, PLoS One. 8:e61540, 2013) and the like.

Examples of the chondrocyte inducer to be used in the present invention include c-Myc, Klf4 and SOX9 (Outani H, et al, PLoS One. 8:e77365, 2013) and the like.

Examples of the hepatocyte inducer to be used in the present invention include FOXA3, HNF1A and HNF4A (Huang P, et al, Cell Stem Cell. 14:370-384, 2014) and the like.

Examples of the melanocyte inducer to be used in the present invention include MITF, SOX10 and PAX3 (Yang R, et al, Nat Commun. 5:5807, 2014) and the like.

Examples of the hematopoietic progenitor cell inducer to be used in the present invention include ERG, GATA2, LMO2, RUNX1c and SCL (Batta K, Cell Rep. 9:1871-84, 2014) and the like.

Examples of the erythroblast inducer to be used in the present invention include c-MYC and BCL-XL (Hirose S, et al, Stem Cell Reports. 1:499-508, 2013) and the like.

Examples of the megakaryocyte progenitor cell inducer to be used in the present invention include BMI1, c-MYC and BCL-XL (Nakamura S, et al, Cell Stem Cell. 14:535-548, 2014) and the like.

In the present invention, when the cell regulatory factor is in the form of a protein, a method of introducing the cell regulatory factor into the cell may be, for example, lipofection, fusion with cell membrane permeable peptide (e.g., HIV-derived TAT and polyarginine), microinjection and the like.

On the other hand, when the cell regulatory factor is in the form of DNA, for example, it can be introduced into the somatic cell by a means using vector such as virus, plasmid, artificial chromosome and the like, lipofection, liposome, microinjection and the like. Examples of the virus vector include retrovirus vector, lentivirus vector (all the above: Cell, 126, pp. 663-676, 2006; Cell, 131, pp. 861-872, 2007; Science, 318, pp. 1917-1920, 2007), adenovirus vector (Science, 322, 945-949, 2008), adeno-associated virus vector, Sendaivirus vector (WO 2010/008054) and the like. Examples of the artificial chromosome vector include human artificial chromosome (HAC), yeast artificial chromosome (YAC), bacterium artificial chromosome (BAC, PAC) and the like. As the plasmid, a plasmid for mammalian cell can be used (Science, 322:949-953, 2008). The vector may contain a regulatory sequence such as promoter, enhancer, ribosome-binding sequence, terminator, polyadenylated site and the like to enable expression of a nuclear reprogramming substance. Where necessary, moreover, it may contain the aforementioned selection marker sequence such as drug resistance gene, thymidine kinase gene, diphtheriatoxin gene and the like, reporter gene sequence such as fluorescence protein (GFP etc.), β-glucuronidase (GUS), FLAG and the like, and the like.

When the cell regulatory factor is in the form of RNA, for example, it may be introduced into the somatic cell by a means such as lipofection, microinjection and the like and RNA incorporating 5-methylcytidine and pseudouridine (TriLink Biotechnologies) to suppress degradation may also be used (Warren L, (2010) Cell Stem Cell. 7:618-630).

The cancer cell after introduction of a cell regulatory factor can be cultured in a culture medium prepared using a medium for culturing animal cells as a basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium and mixed medium of these and the like. The medium may contain serum or serum-free. Where necessary, the medium may also contain one or more substances from, for example, albumin, insulin, transferrin, selenium, fatty acid, trace element, 2-mercaptoethanol, thiolglycerol, lipid, amino acid, L-glutamine, non-essential amino acid, vitamin, growth factor, low-molecular-weight compound, antibiotic, antioxidant, pyruvic acid, buffering agent, inorganic salt, cytokine and the like.

In other embodiment of the present invention, the cancer cell after introduction of a cell regulatory factor can also be cultured in a culture medium appropriately selected to meet the property of the cell regulatory factor, and examples of the conditions therefor are shown in the following.

When the cell regulatory factor is a reprogramming factor, examples of the culture medium for the cell after reprogramming include DMEM, DMEM/F12 and DME culture medium (these culture media optionally further containing LIF, penicillin/streptomycin, puromycin, L-glutamine, non-essential amino acids, β-mercaptoethanol and the like as appropriate) containing 10-15% FBS, and a commercially available culture medium (e.g., culture medium for mouse ES cell culture (TX-WES culture medium, Thromb-X), culture medium for primates ES cell culture (culture medium for primate ES/iPS cell, ReproCELL Incorporated), serum-free medium (mTeSR, Stemcell Technology)) and the like.

An example of the culture method of the cell after reprogramming includes contacting the somatic cell and a reprogramming factor in 10% FBS-containing DMEM or DMEM/F12 culture medium at 37° C. in the presence of 5% $CO_2$, culturing the cells for about 4-7 days, reseeding the cells on feeder cells (e.g., mitomycin C-treated STO cell, SNL cell etc.), and culturing the cells in a bFGF-containing culture medium for primate ES cell culture from about 10 days after the contact of the somatic cell and the reprogramming factor contact, whereby an iPS-like colony can be formed about 30-about 45 days or longer from the contact. Alternatively, by culturing on feeder cells (e.g., mitomycin C-treated STO cell, SNL cell etc.) at 37° C. in the presence of 5% $CO_2$ in a 10% FBS-containing DMEM culture medium (optionally further containing LIF, penicillin/streptomycin, puromycin, L-glutamine, non-essential amino acids, β-mercaptoethanol and the like as appropriate), an ES-like colony can be formed about 25-about 30 days or more later. Desirably, a method using the reprogrammed somatic cell itself (Takahashi K, et al. (2009), PLoS One. 4:e8067 or WO2010/137746) or an extracellular matrix (e.g., Laminin-5 (WO2009/123349) and Matrigel (BD)), instead of the feeder cell, can be exemplified.

Besides this, a method of culturing in a medium without serum can also be exemplified (Sun N, et al. Proc Natl Acad Sci USA. 106:15720-15725, 2009 or Nakagawa M, et al, Sci Rep. 4:3594, 2014). Furthermore, to increase establishment efficiency, iPS cell may be established under hypoxic conditions (oxygen concentration of not less than 0.1%, not more than 15%) (Yoshida Y, et al. (2009), Cell Stem Cell. 5:237-241 or WO2010/013845).

When the cell regulatory factor is a nerve cell inducer, examples of the culture medium and culture conditions for cells after introduction of the factor include those described in WO2014/148646, Wapinski O L et al, Cell. 155:621-635, 2013 and the like.

When the cell regulatory factor is a neural stem cell inducer, examples of the culture medium and culture conditions for cells after introduction of the factor include those described in Han D W et al, Cell Stem Cell. 10:465-472, 2012 and the like.

When the cell regulatory factor is a neural crest cell inducer, examples of the culture medium and culture conditions for cells after introduction of the factor include those described in Kim Y J, et al, Cell Stem Cell. 15:497-506, 2014 and the like.

When the cell regulatory factor is a myocardial cell inducer, examples of the culture medium and culture conditions for cells after introduction of the factor include those described in Ieda M et al, Cell. 142:375-386, 2010 and the like.

When the cell regulatory factor is a muscle cell inducer, examples of the culture medium and culture conditions for cells after introduction of the factor include those described in Tanaka A, et al, PLoS One. 8:e61540, 2013 and the like.

When the cell regulatory factor is a chondrocyte inducer, examples of the culture medium and culture conditions for cells after introduction of the factor include those described in Outani H, et al, PLoS One. 8:e77365, 2013 and the like.

When the cell regulatory factor is a hepatocyte inducer, examples of the culture medium and culture conditions for cells after introduction of the factor include those described in Huang P, et al, Cell Stem Cell. 14:370-384, 2014 and the like.

When the cell regulatory factor is a melanocyte inducer, examples of the culture medium and culture conditions for cells after introduction of the factor include those described in Yang R, et al, Nat Commun. 5:5807, 2014 and the like.

When the cell regulatory factor is a hematopoietic progenitor cell inducer, examples of the culture medium and culture conditions for cells after introduction of the factor include those described in Batta K, Cell Rep. 9:1871-84, 2014 and the like.

When the cell regulatory factor is an erythroblast inducer, examples of the culture medium and culture conditions for cells after introduction of the factor include those described in Hirose S, et al, Stem Cell Reports. 1:499-508, 2013 and the like.

When the cell regulatory factor is a megakaryocyte progenitor cell inducer, examples of the culture medium and culture conditions for cells after introduction of the factor include those described in Nakamura S, et al, Cell Stem Cell. 14:535-548, 2014 and the like.

Test Substance

In the screening method of the present invention, any test substance can be used, which may be any known compound or novel compound. For example, cell extract, cell culture supernatant, microorganism fermentation product, extract derived from marine organism, plant extract, purified protein or crude protein, peptide, non-peptide compound, synthesized low-molecular-weight compound, natural compound and the like can be mentioned. In the present invention, the test substance can also be obtained using any of many approaches in the combinatorial library method known in the technical field including (1) biological library method, (2) synthetic library method using deconvolution, (3) "one-bead one-compound" library method, and (4) synthetic library method using affinity chromatography selection. While a biological library method using affinity chromatography selection is limited to peptide library, other 4 approaches are applicable to peptide, non-peptide oligomer, and low-molecular-weight compound library of the compound (Lam (1997) Anticancer Drug Des. 12: 145-67). Examples of the synthesis method of molecule library can be found in the technical field (DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). Compound library can be produced as a solution (refer to Houghten (1992) Bio/Techniques 13: 412-21) or bead (Lam (1991) Nature 354: 82-4), chip (Fodor (1993) Nature 364: 555-6), bacterium (U.S. Pat. No. 5,223,409), spore (U.S. Pat. Nos. 5,571,698, 5,403,484, and 5,223,409), plasmid (Cull et al. (1992) Proc. Natl. Acad. Sci. USA 89: 1865-9) or phage (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US-B-2002103360).

A cancer cell can be preferably contacted with a test substance by culturing the cancer cell introduced with a cell regulatory factor as mentioned above in a culture medium added with the test substance. The concentration of the test substance added to the culture medium can be appropriately selected as long as it does not adversely influence the cell growth. It is generally 0.1-100 nM. The time of start of the contact is, for example, immediately after introduction of the cell regulatory factor to several days thereafter. When an exogenous cell regulatory factor is introduced in an expression regulatable (ON/OFF possible) form into the cancer cell, the contact can be started simultaneously with an expression ON treatment or within several days from the treatment. While the contact period is not particularly limited as long as it is sufficient for observation of change of the cancer cell, the factor is generally placed in coexistence in the culture medium until a positive colony emerges.

Change of Cancer Cell

In the method of screening for a therapeutic drug for cancer of the present invention, change of cell caused by expression of an exogenous cell regulatory factor under contact with a test substance in a cancer cell can be used as an index. In the present invention, change of the cancer cell depends on the cell regulatory factor to be introduced.

When the cell regulatory factor is a reprogramming factor, the change of the cell is reprogramming of cancer cell. As used herein, the reprogramming is used as a concept encompassing not only complete reprogramming (i.e., establishment of iPS cell having stable pluripotency and undifferentiated state) but also change into a more undifferentiated state as compared to the original cancer cell (even when the cell regulatory factor is a factor induced to directly differentiate into other cell not via reprogramming, it similarly encompasses not only complete differentiation into the object cell, but also change into a state acquiring more characteristics of the object cell as compared to the original cancer cell). Therefore, reprogramming of cancer cell can be evaluated using colony formation, expression of undifferentiation-specific antigen, or expression of undifferentiation-specific gene as an index. Examples of the undifferentiation-specific gene include a gene showing specific expression in embryonic stem cells, a gene suggested to have an important role in the maintenance of pluripotency and the like. Such genes are described in Cell. 2005 Sep. 23; 122(6):947-56, Stem Cells. 2004; 22(1):51-64., Mol Biol Cell. 2002 April; 13(4):1274-81., Mol Reprod Dev. 2000 June; 56(2):113-23., EMBO J. 1998 Apr. 1; 17(7):2019-32., Proc Natl Acad Sci USA. 2003 Nov. 11; 100(23):13350-5., Development. 2005 March; 132(5):885-96., Blood. 2005 Jan. 15; 105(2):635-7., Cell. 2003 May 30; 113(5):631-42., J Biol Chem. 2000 Mar. 3; 275(9):6608-19., Mol Cell Biol. 2005 May; 25(9):3492-505., Mech Dev. 2004 March; 121 (3):237-46. and WO2007/069666. Concrete examples of undifferentiation-specific gene include, but are not particularly limited to, Nanog, Epcam, Cdh1, Fboxo15, PODXL, Oct3/4, Sox2 and GDF3. Examples of undifferentiation-specific antigen include, but are not limited to, antigen selected from the group consisting of SSEA-1, SSEA-3, SSEA-4, TRA-2-54, TRA-1-60 and TRA-1-80. In human, since SSEA-1 is not detected in undifferentiated cells, SSEA-3 and SSEA-4 are preferably used instead of SSEA-1.

While it is not particularly limited, colony formation is evaluated by the number thereof measured under a microscope. The measurement may be performed mechanically (WO2011/010449), or visually observed. On the other hand, the cell expressing an undifferentiation-specific antigen can also be evaluated by the number of cells expressing the antigen by using a cell sorter such as FACS and the like. Expression of undifferentiation-specific gene can be evaluated by the expression level measured by reverse transcriptase PCR analysis, quantitative reverse transcriptase PCR analysis, Northern blot analysis, immunohistochemistry, array analysis, RNA-seq analysis, reporter gene analysis and combinations thereof. Therefore, in the present invention, the change of the cancer cell can be put down differently as increase in the number of cells expressing undifferentiation-specific antigen, increase in the expression level of undifferentiation-specific gene, or formation of colony.

When the cell regulatory factor is a nerve cell inducer, the change of the cancer cell can be evaluated using the expression of nerve cell specific gene as an index. Examples of the nerve cell specific gene include gene selected from the group consisting of MFNG, GRIP1, NGFR, Zfp238, GRINT1 and SYT3 (WO2014/148646 and Wapinski O L et al, Cell. 155:621-635, 2013).

When the cell regulatory factor is a neural stem cell inducer, the change of the cancer cell can be evaluated using the expression of neural stem cell specific gene as an index. Examples of the nerve cell specific gene include gene selected from the group consisting of Olig2, Sox2 and Mash1/Ascl1 (Han D W et al, Cell Stem Cell. 10:465-472, 2012).

When the cell regulatory factor is a neural crest cell inducer, the change of the cancer cell can be evaluated using the expression of neural crest cell specific gene as an index. Examples of the neural crest cell specific gene include gene selected from the group consisting of TWIST1, SNAIL2, ITGA4, ITGA6, SOX5, SOX6, PLP1 and Myelin Protein Zero [MPZ] (Kim Y J, et al, Cell Stem Cell. 15:497-506, 2014).

When the cell regulatory factor is a myocardial cell inducer, the change of the cancer cell can be evaluated using the expression of myocardial cell specific gene as an index. Examples of the myocardial cell specific gene include αMHC and cTnT (Ieda M et al, Cell. 142:375-386, 2010).

When the cell regulatory factor is a muscle cell inducer, the change of the cancer cell can be evaluated using the expression of muscle cell specific gene as an index. Examples of the muscle cell specific gene include gene selected from the group consisting of myogenin, myosin heavy chain (MHC), MEF2C and SIX1 (Tanaka A, et al, PLoS One. 8:e61540, 2013).

When the cell regulatory factor is a chondrocyte inducer, the change of the cancer cell can be evaluated using the expression of chondrocyte specific gene as an index. Examples of the chondrocyte specific gene include gene selected from the group consisting of COL11A2, COL2A1 and ACAN (Outani H, et al, PLoS One. 8:e77365, 2013).

When the cell regulatory factor is a hepatocyte inducer, the change of the cancer cell can be evaluated using the expression of hepatocyte specific gene as an index. Examples of the hepatocyte specific gene include gene selected from the group consisting of albumin (ALB), α-1-antitrypsin (AAT), CYP1A2, CYP2A6, CYP2B6, CYP2C8, CYP2C9 and CYP3A4 (Huang P, et al, Cell Stem Cell. 14:370-384, 2014).

When the cell regulatory factor is a melanocyte inducer, the change of the cancer cell can be evaluated using the expression of melanocyte specific gene as an index. Examples of the melanocyte specific gene include gene selected from the group consisting of TYR, TYRP1 and DCT (Yang R, et al, Nat Commun. 5:5807, 2014).

When the cell regulatory factor is a hematopoietic progenitor cell inducer, the change of the cancer cell can be evaluated using the expression of hematopoietic progenitor cell specific gene as an index. Examples of the hematopoietic progenitor cell specific gene include gene and antigen selected from the group consisting of CD31, CD41, c-KIT, CD45, CD11b and TER119 (Batta K, Cell Rep. 9:1871-84, 2014).

When the cell regulatory factor is a erythroblast inducer, the change of the cancer cell can be evaluated using the expression of erythroblast specific gene as an index. Examples of the erythroblast specific gene include gene and antigen selected from the group consisting of GPA, CD71, GATA1 and RAF1 (Hirose S, et al, Stem Cell Reports. 1:499-508, 2013).

When the cell regulatory factor is a megakaryocyte progenitor cell inducer, the change of the cancer cell can be evaluated using the expression of megakaryocyte progenitor cell specific gene as an index. Examples of the megakaryocyte progenitor cell specific gene include gene and antigen selected from the group consisting of CD41a, CD42a, CD42b and CD9 (Nakamura S, et al, Cell Stem Cell. 14:535-548, 2014).

When each of the aforementioned cell specific genes is used as an index for screening in the present invention, the cell expressing the gene can also be evaluated by the cell number by using a cell sorter such as FACS and the like, or can also be evaluated by the expression level measured by reverse transcriptase PCR analysis, quantitative reverse transcriptase PCR analysis, Northern blot analysis, immunohistochemistry, array analysis, reporter gene analysis and combinations thereof. Therefore, in the present invention, "increase in the change of the cancer cell" can be put down differently as increase in the number of cells expressing the gene, or increase in the expression level of the gene.

Kit for Screening for Therapeutic Drug for Cancer

In the present invention, the kit for screening for a therapeutic drug for cancer contains the aforementioned cell regulatory factor.

In the present invention, the kit for screening for a therapeutic drug for cancer may further contain a document or instruction describing production procedure of cell regulation, and measurement method and procedure of index. It may further contain a panel of various carcinoma cells having different effective target proteins (effective target protein is as defined above), or can further contain an antibody against cellular surface antigen or nucleic acid for detection of cell specific gene to be the index of the change of the above-mentioned cancer cell.

In another aspect of the present invention, an identification method of a protein that can be a drug discovery target for a therapeutic drug for cancer is provided. The identification method characteristically includes the following steps:

(i) a step of expressing an exogenous cell regulatory factor in a cancer cell comprising a gene encoding a test protein in an expression regulatable form, under conditions resulting in the expression of a candidate gene or under conditions suppressing expression of the gene, (ii) a step of confirming change in the cancer cell, and (iii) a step of selecting the test protein as a protein capable of becoming a drug discovery target of a therapeutic drug for cancer, when the change of the cancer cell increased under conditions suppressing expression of the gene, as compared to that under conditions resulting in the expression of the candidate gene.

As used herein, the candidate gene is, for example, a gene specifically expressed in a cancer cell or a gene highly expressed in a cancer cell, which is identified by comprehensively analyzing the gene expression in the cancer cell by microarray and the like.

As used herein, moreover, the expression regulatable form means a form in which ON/OFF of the expression of the candidate gene is possible and, for example, an expression vector and the like in which candidate gene is placed under regulation of induction promoter (e.g., metallothionein promoter (induced by heavy metal ion), heat-shock protein promoter (induced by heat shock), Tet-ON/Tet-OFF system promoter (induced by addition or removal of tetracycline or a derivative thereof), steroid-responsive promoter (induced by steroid hormone or a derivative thereof) etc.) can be mentioned.

The cell regulatory factor, change of cancer cell, and index and the like for confirmation and evaluation of the change are the same as those in the above-mentioned screening method for a therapeutic drug for cancer.

While the present invention is explained further specifically in the following Examples, the scope of the present invention is not limited in any manner by the Examples.

Example 1

To investigate effects of cancer gene on the reprogramming of cancer cells, a mouse sarcoma cell line described in Yamada K, et al, J Clin Invest. 123:600-610, 2013 (to be also referred to as G1297 cell line) capable of inducing the EWS/ATF1 fusion gene depending on doxycycline (Dox) was used. The sarcoma cell was confirmed to show arrest of proliferation in vitro and tumor regression in vivo by discontinuation of EWS/ATF1 expression.

Figure 3:
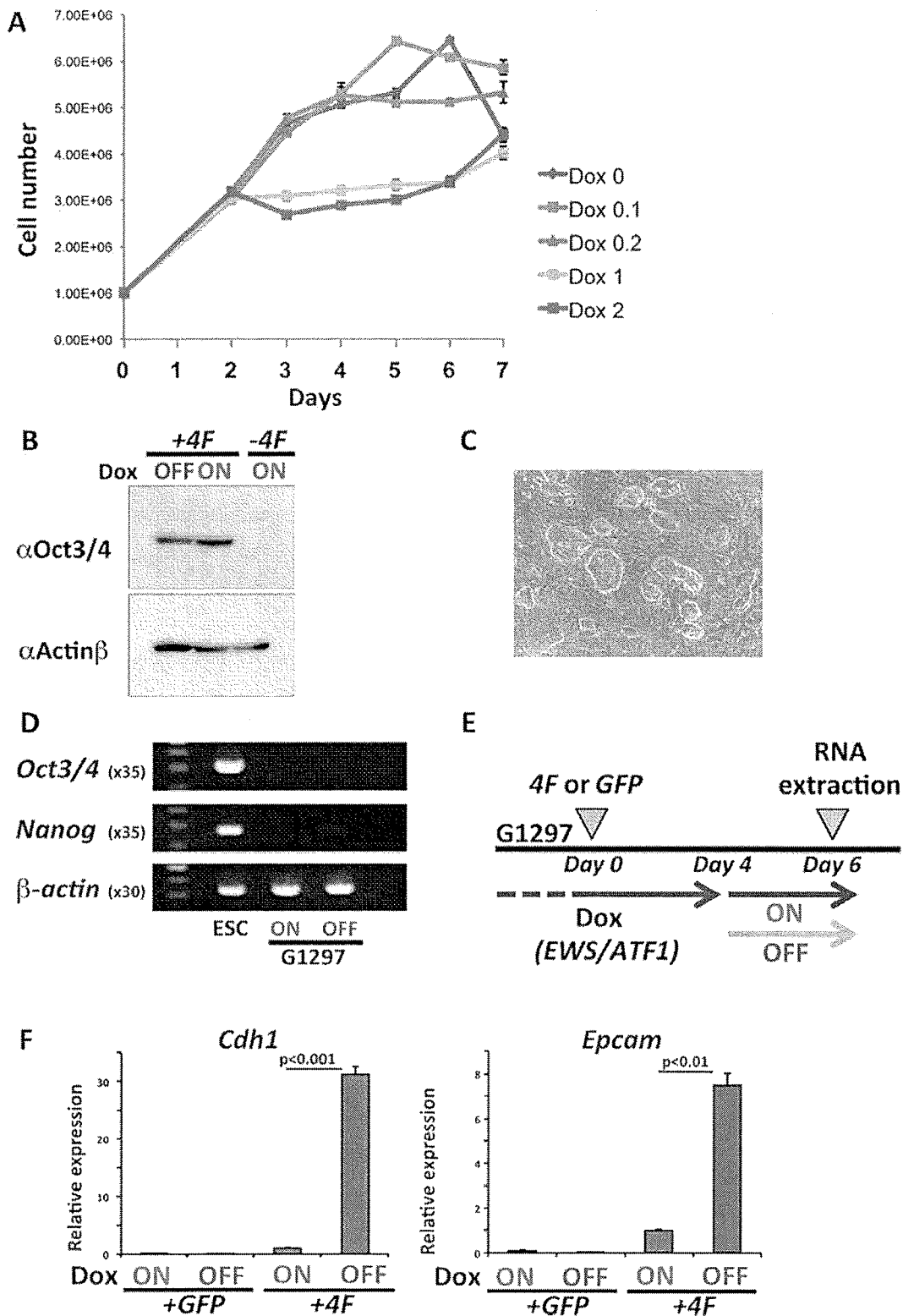
FIG. 3A shows proliferation curves when sarcoma cell line G1297 was cultured with the addition of 0, 0.1, 0.2, 1 or 2 μg/ml doxycycline (DOX).
FIG. 3B shows the measurement results of Oct3/4 level by Western blotting method when a reprogramming factor was introduced (+4F) or was not introduced (−4F) into sarcoma cell line G1297, and the expression of EWS/ATF1 was induced (ON) or was not induced (OFF).
FIG. 3C shows a phase contrast microscopic image of iPS cells established after introduction of a reprogramming factor when EWS/ATF1 expression was not induced (DOX 0 μg/ml).
FIG. 3D shows the measurement level of Oct3/4 and Nanog by RT-PCR method, when the expression of EWS/ATF1 was induced (ON) or was not induced (OFF) in sarcoma cell line G1297. In the Figure, ESC (ES cell) was used as a positive control.
FIG. 3E is a schematic drawing describing induction of EWS/ATF1 expression and a method of introducing a reprogramming factor.
FIG. 3F shows the measurement results of the expression of Cadh1 (left Figure) and Epcam (right Figure) in cells by RT-PCR when a reprogramming factor was introduced (+4F) or was not introduced (GFP) into sarcoma cell line G1297, and the expression of EWS/ATF1 was induced (ON) or was not induced (OFF).

EWS/ATF1 was confirmed to show no influence on the expression level of the introduced reprogramming factor because induction of EWS/ATF1 expression by the addition of 0.2 µg/ml doxycycline did not influence proliferation of mouse ES cells (FIG. 3A, FIG. 3B and FIG. 3D).

Then, whether introduction of a reprogramming factor into G1297 causes reprogramming of G1297 was confirmed. In the sarcoma cell expressing EWS/ATF1, iPS cell-like colony was not observed even when the reprogramming factor (4F: Oct3/4, Sox2, Klf4 and c-Myc) was introduced by retrovirus. On the other hand, when the EWS/ATF1 expression was discontinued, iPS cell-like colonies were confirmed by the expression of 4F (FIG. 1A-C). The iPS cell-like cell line was established by picking up the iPS cell-like colonies (FIG. 3C). The iPS cells were induced by the following method. Oct3/4, Sox2, Klf4 and c-Myc were each introduced into Plat-E cells by using a pMXs-based retrovirus vector, and the virus-containing supernatant was recovered and filtered through a 0.45 µm cellulose acetate filter. G1297 was seeded at $8\times10^5$ cells per 60-mm dish, and infected with the virus-containing supernatant. On day 3 after infection, the medium was exchanged with a LIF-containing ES medium and the cells were cultured.

The established iPS cell-like cell line was confirmed to express EWS/ATF1 in a doxycycline-dependent manner, as in the parent sarcoma cell (FIG. 1D). Furthermore, some chromosome abnormalities were similarly observed, and the iPS cell-like cell line was confirmed to have derived from the sarcoma cell (FIG. 1E). The expression of pluripotency-related genes such as Nanog, endogenous Oct3/4 (Pou5f1) and the like in the iPS cell-like cell derived from the sarcoma cell was compared with that in ES cell, and a significant difference was not found (FIG. 1F and FIG. 3D). RT-PCR was performed using the following method. Using RNeasy Plus Mini kit (Qiagen, Hilden, Germany), the total RNA was isolated. Using Go-taq qPCR Master Mix (Promega, Madison, USA), quantitative real-time PCR analysis was performed. The transcription level was standardized based on β-actin or GAPDH value.

The efficiency of reprogramming of the sarcoma cell was 0.06%, which is lower than the reprogramming efficiency of MEF. The obtained iPS cell-like cell was subcutaneously administered to immunodeficient mice. As a result, teratoma was formed, and chimera mice could be created by injecting the cell to the blastocyst (FIG. 1G and FIG. 1H).

From the above, it was confirmed that pluripotent cells can be obtained by reprogramming EWS/ATF1 expression dependent sarcoma cells, by suppressing expression of EWS/ATF1. The results indicate that EWS/ATF1 acts suppressively in reprogramming EWS/ATF1 expression dependent sarcoma cells.

Example 2

Successively, the mechanism of defective reprogramming of cancer cells via EWS/ATF1 was analyzed. First, phenomena in the early stages of reprogramming were confirmed by FACS analysis of the development of SSEA1 positive cells (FIG. 1I). As a result, it was confirmed that the number of SSEA1 positive cells decreases in a Dox concentration dependent manner. This suggests that EWS/ATF1 inhibits reprogramming from the early stages of reprogramming. In addition, expression of a marker of mesenchyme-epithelial transfer, which is the initial event in the reprogramming of fibroblast, was examined by microarray. As a result, it was confirmed that, after suppression of EWS/ATF1 expression, these genes increase significantly. On the other hand, since expression of EWS/ATF1 does not suppress development of SSEA1 positive cells by reprogramming of MEF (FIG. 1J), it was suggested that expression of EWS/ATF1 causes reprogramming suppression specific to sarcoma cells.

To examine the influence exerted by the expression of oncogene on the transcription response upon 4F introduction, microarray analyses of sarcoma cell with introduction of 4F (4F-sarcoma cell) and sarcoma cell with introduction of GFP as a negative control were performed with or without EWS/ATF1 expression (FIG. 3E). The microarray analysis was performed using Mouse Gene 1.0 ST Array (Affymetrix Inc., Santa Clara, USA). All data were analyzed using GeneSpring GX software program (version 12; Agilent Technology, Santa Clara, USA).

As a result, it was confirmed that many genes increase or decrease by the suppression of EWS/ATF1 expression in 4F-sarcoma cell (FIG. 1K). The genes with expression change similarly increased or decreased also in 4F-sarcoma cell with EWS/ATF1 expression; however, the difference in the change was small as compared to 4F-sarcoma cell without EWS/ATF1 expression (FIG. 3F). From the above, it was suggested that EWS/ATF1 expression suppresses fate change of the sarcoma cell.

Example 3

Furthermore, an influence of EWS/ATF1 expression on the induction of differentiation of skeletal muscle by the introduction of MYOD1 was examined (FIG. 1L). As a result, it was confirmed that expression of Myogenin (MYOG), which is an initial skeletal muscle differentiation marker, was significantly upregulated in MYOD1-introduced sarcoma cell (MYOD1-sarcoma cell) after suppression of EWS/ATF1 expression (FIG. 1M). In addition, MHC (myosin heavy chain) positive cells significantly increased in MYOD1-sarcoma cell without EWS/ATF1 expression (FIG. 1N). The initial transcription response by the introduction of MYOD1 was analyzed by the microarray method. As a result, the number of gene change by the introduction of MYOD1 increased in the cell without EWS/ATF1 expression as compared to the sarcoma cell with EWS/ATF1 expression (FIG. 1O). It was shown that a skeletal muscle differentiation induction-related gene (e.g., Myogenin) is markedly upregulated by the introduction of MYOD1 in the sarcoma cell with suppression of EWS/ATF1 expression. On the other hand, it was confirmed that differentiation transformation of muscle cell is suppressed by EWS/ATF1 expression.

The above results suggest that EWS/ATF1 expression restricts transcription response to an exogeneous transcription factor that changes the cell fate.

Example 4

Then, the effect of EWS/ATF1 expression on the reprogramming of human clear cell sarcoma (CCS) cell line was examined. When EWS/ATF1 was knocked down in CCS cell introduced with 4F (FIG. 2A), the expression of PODXL encoding TRA-1-60, which is an initial marker of human reprogramming, increased (FIG. 2B); however, a completely reprogrammed iPS cell could not be established.

Figure 2:
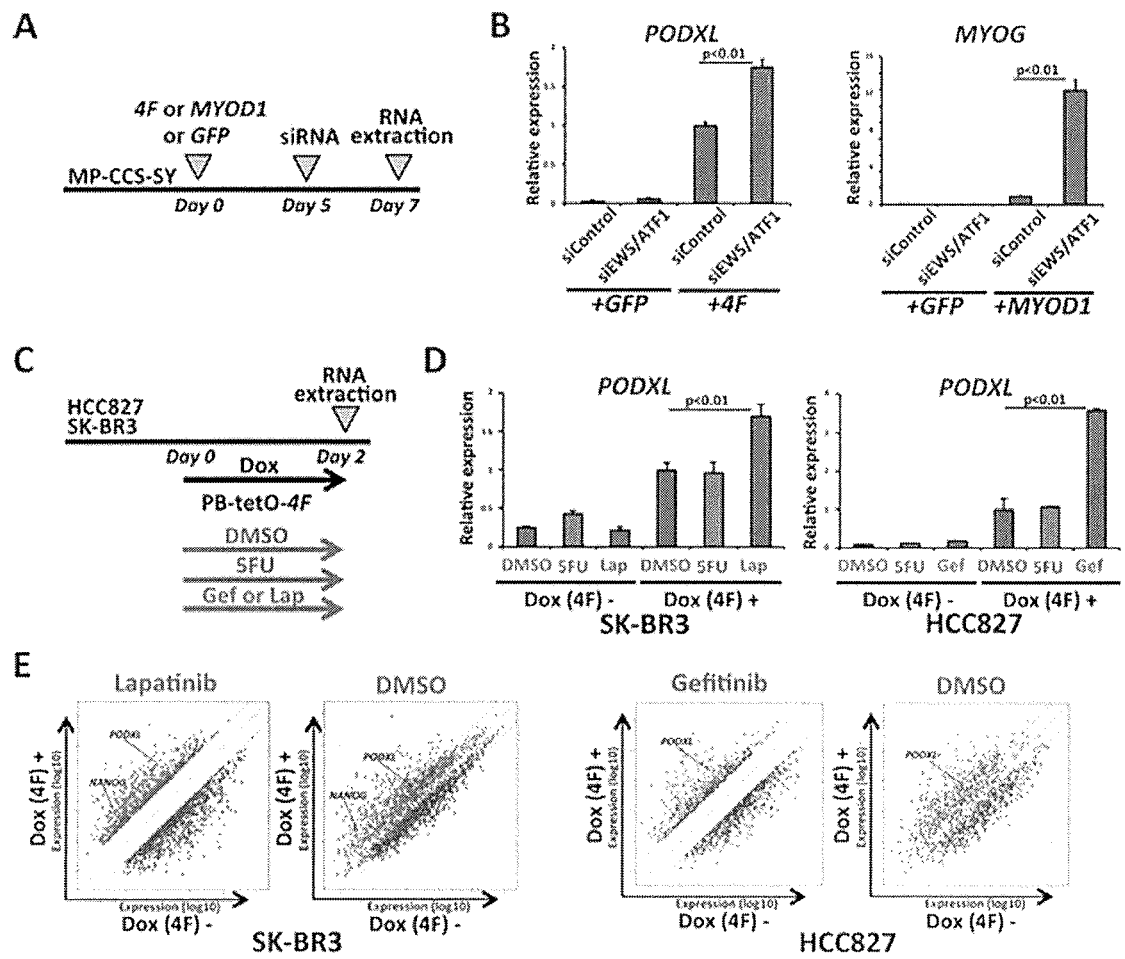
FIG. 2A is a schematic drawing describing a method of introducing reprogramming factor, MYOD1 or GFP and siRNA into MP-CCS-SY cell line.
FIG. 2B shows the measurement results of the expression of PODXL by RT-PCR when reprogramming factor (+4F) or GFP was introduced into MP-CCS-SY cell line, and EWS/ATF1 expression was suppressed by RNAi (siEWS/ATF1) or was not suppressed (siControl) (left Figure); and the measurement results of the expression of Myogenin by RT-PCR when MYOD1 or GFP was introduced into MP-CCS-SY cell line, and EWS/ATF1 expression was suppressed by RNAi (siEWS/ATF1) or was not suppressed (siControl) (right Figure).
FIG. 2C is a schematic drawing describing introduction of a reprogramming factor into HCC827 or SK-BR3 cell line and a method of addition of each medicament.
FIG. 2D shows the measurement results of the expression of PODXL by RT-PCR, when a reprogramming factor was introduced (Dox(4F)+) or was not introduced (Dox(4F)−) into SK-BR3 cell line and DMSO, 5FU or Lapatinib (Lap) was added (left Figure); and the measurement results of the expression of PODXL by RT-PCR, when a reprogramming factor was introduced (Dox(4F)+) or was not introduced (Dox(4F)−) into HCC827 cell line and DMSO, 5FU or Gefitinib (Gef) was added (right Figure).
FIG. 2E shows the results of microarray analysis when a reprogramming factor was introduced (Dox(4F)+) or was not introduced (Dox(4F)−) into SK-BR3 cell line and Lapatinib (Lap) or DMSO was added (left Figure), and the results of microarray analysis when a reprogramming factor was introduced (Dox(4F)+) or was not introduced (Dox(4F)−) into HCC827 cell line and Gefitinib (Gef) or DMSO was added (right Figure).

Similarly, when EWS/ATF1 was knocked down in CCS cell introduced with MYOD1, MYOG expression increased (FIG. 2B).

Example 5

Figure 4:
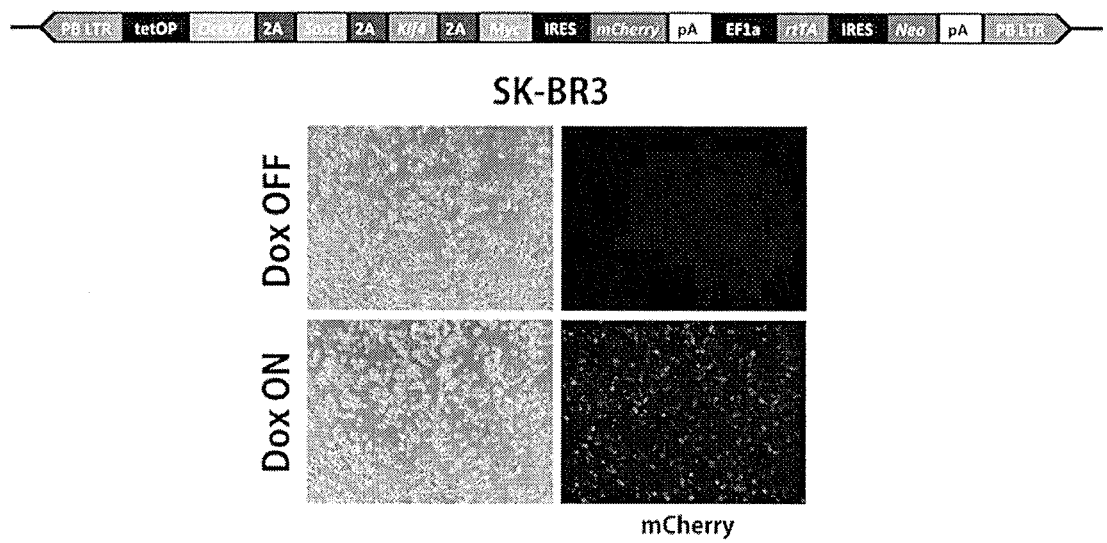
FIG. 4A shows a construct of PiggyBac vector for introducing a reprogramming factor and phase difference images and fluorescence images of the cells after introduction into SK-BR3.
FIG. 4B shows the measurement results of the expression of PODXL by RT-PCR when a reprogramming factor was introduced (Dox(4F)+) or was not introduced (Dox(4F)−) into A549 cell line, and DMSO, 5FU (1 mM or 10 mM) or Gefitinib (Gef) (10 mM or 50 mM) was added.
Figure 4:
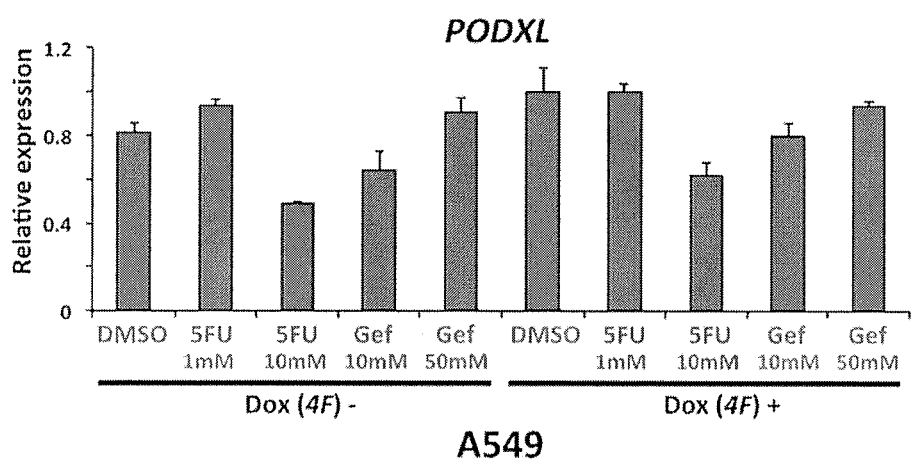

Besides the above, an influence of the activation of oncogene signal on cell reprogramming was examined. Epithelial growth factor receptor (EGFR) mutated lung cancer cell line HCC827 and HER2-amplified breast cancer cell line SK-BR3 were used for the experiment. These cancer cell lines are sensitive to EGFR specific tyrosine kinase and HER2 tyrosine kinase inhibitor, respectively. Dox-inducing 4F was introduced into HCC827 and SK-BR3 by using PB transposon (FIG. 4A), and the effect of EGFR tyrosine kinase inhibitor gefitinib, and HER2 tyrosine kinase inhibitor lapatinib on the reprogramming was examined respectively (FIG. 2C). As a result, when 4F-introduced SK-BR3 was treated with 50% inhibitory concentration ($IC_{50}$) of lapatinib, expression of reprogramming marker PODXL was promoted (FIG. 2D); however, establishment of a completely reprogrammed iPS cell from a human cancer cell line was unsuccessful. On the other hand, PODXL expression did not increase by a treatment with $IC_{50}$ concentration of 5-fluorouracil (5FU) (FIG. 2D). Similarly, a treatment of HCC827 introduced with 4F with $IC_{50}$ concentration of gefitinib promoted PODXL expression, whereas a treatment with $IC_{50}$ concentration of 5FU did not increase PODXL expression (FIG. 2D). On the other hand, in lung cancer cell line A549 having wild-type EGFR, a gefitinib treatment upon 4F introduction did not increase PODXL (FIG. 4B). Change of gene expression with or without introduction of 4F into HCC827 and SK-BR3 was examined by microarray analysis. It was clarified that many genes including PODXL and NANOG were upregulated or downregulated when they were treated with gefitinib and lapatinib (FIG. 2E). These results suggest that major cancer gene signals maintain characteristics of cancer cells via a stable transcription network.

Example 6

Figure 5:
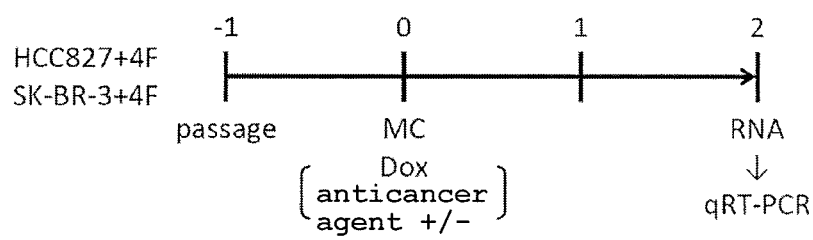
FIG. 5A is a schematic drawing describing induction of a reprogramming factor by the addition of Dox to HCC827 and SK-BR3, and a method of introducing an anticancer agent (Gefitinib, Imatinib, Lapatinib, 5-FU).
FIG. 5B shows the results of transcription level standardized by GAPDH value from the measurement of the expression of Nanog and GDF3 by RT-PCR when a reprogramming factor was introduced into HCC827 and SK-BR3 (Dox(4F)+), and Gefitinib (0 µM (DMSO added), 0.005 µM or 0.05 µM), Imatinib (0 µM (DMSO added), 1 µM or 10 µM), Lapatinib (0 µM (DMSO added), 0.05 µM or 0.5 µM) or 5-FU (0 µM (DMSO added), 10 µM or 50 µM) was added.
Figure 5:
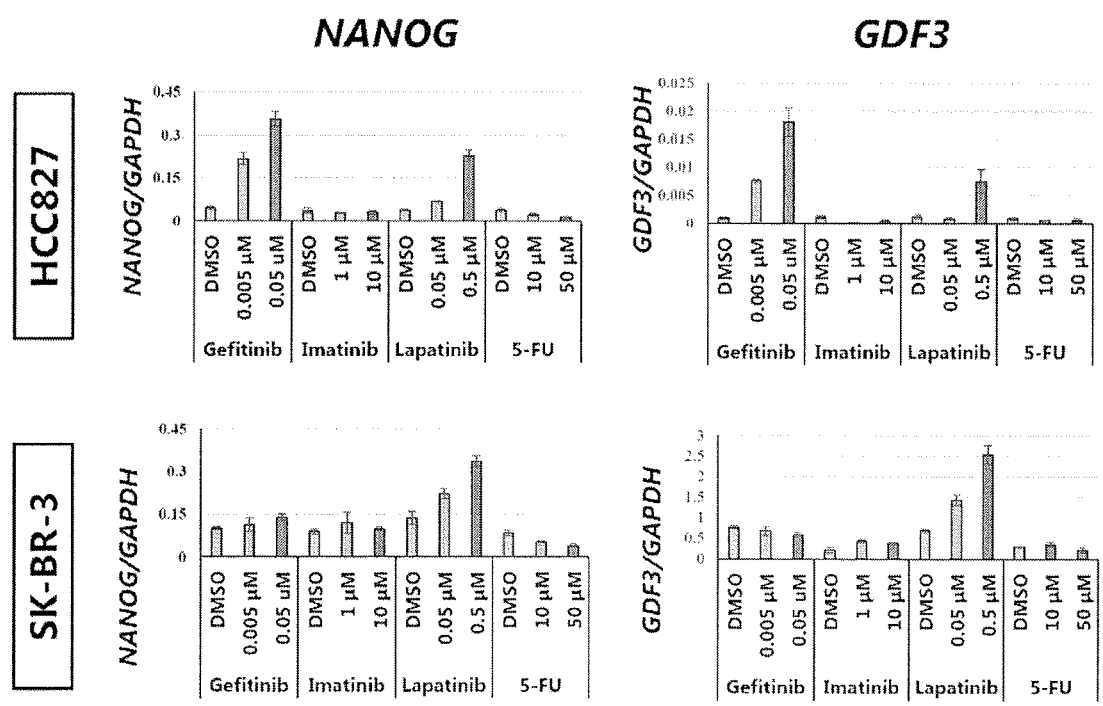

Using a combination of a cancer cell sensitive to a certain kind of anticancer agent and a cancer cell not sensitive to a certain kind of anticancer agent, an influence of a drug-specific cell on the reprogramming was examined. It is known that epithelial growth factor receptor (EGFR) mutation lung cancer cell line HCC827 is sensitive to EGFR tyrosine kinase inhibitor Gefitinib and HER2 tyrosine kinase inhibitor Lapatinib, and that HER2-amplified breast cancer cell line SK-BR3 is sensitive to Lapatinib. A piggyBac vector capable of inducing 4F expression in a Dox inductive manner was introduced into HCC827 line and SK-BR3 line by using piggyBac transposage, expression was induced by Dox, and Gefitinib and Bcr-Abl tyrosine kinase inhibitors (Imatinib, Lapatinib, 5-FU) were added. Two days later, RNA was extracted from the cells, and the expression levels of NANOG and GDF3 were measured by quantitative RT-PCR (FIG. 5A). The results are shown in FIG. 5B. In the HCC827 cell line treated with 0.005 μM or 0.05 μM Gefitinib, or 0.5 μM Lapatinib, the expression of undifferentiation-specific genes NANOG and GDF3 was promoted. On the other hand, a treatment with Imatinib or 5-FU did not promote expression of NANOG and GDF3. In SK-BR3 cell line, the expression of NANOG and GDF3 was promoted only when the cells were treated with 0.05 μM or 0.5 μM Lapatinib. These results show that the reprogramming of cancer cell is promoted in a manner specific to a drug having sensitivity, and the screening method of the present invention is suggested to be a method capable of selectively affording only an effective drug.

Example 7

Figure 6:
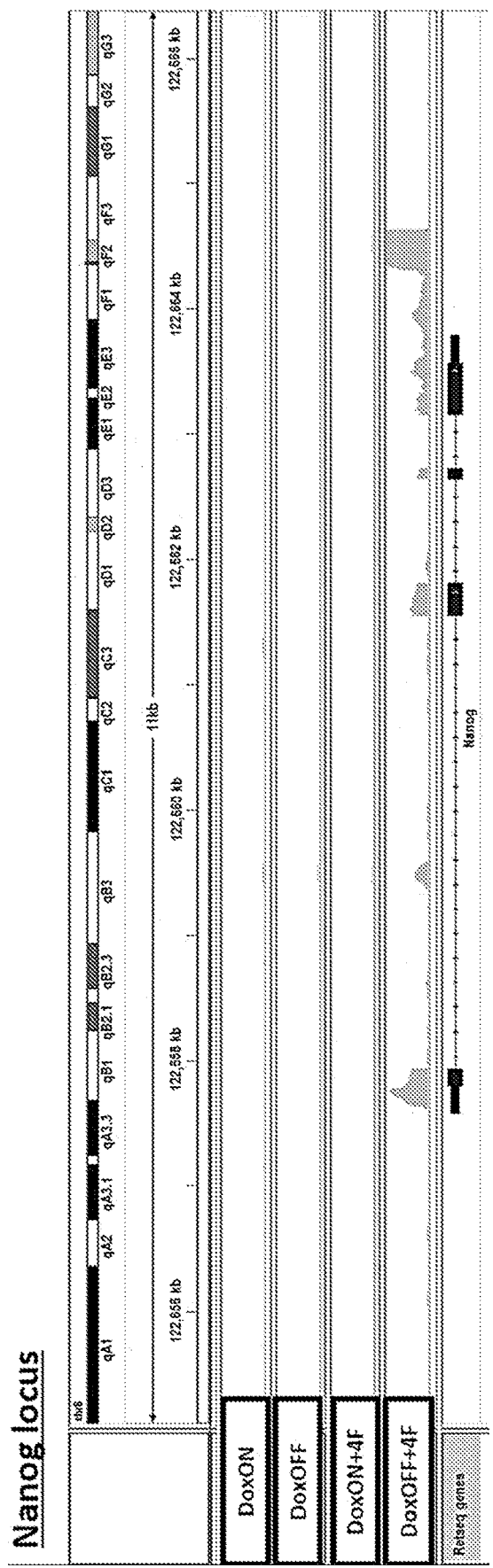
FIG. 6 shows the results of RNA-seq analysis of Nanog gene locus of chromosome 6 when the expression of EWS/ATF1 was induced (DoxON) or was not induced (DoxOFF) in mouse sarcoma cell line G1297, and reprogramming factor was introduced (+4F) or was not introduced.

Moreover, expression of Nanog was measured by a method other than quantitative RT-PCR. The experiment procedures are the same as those in the schematic drawing of FIG. 3E. A reprogramming factor (+4F) or GFP was introduced by retrovirus into G1297 cell line with EWS/ATF1 expression by the addition of Dox, and the expression of Nanog in the cells in which Dox addition was discontinued on day 4 after introduction (DoxOFF) and the cells in which Dox addition was continued (DoxON) was examined by RNA-seq analysis. The results are shown in FIG. 6. It was confirmed that the expression of Nanog gene increases in the DoxOFF+4F cells, namely, the expression of Nanog gene increases by suppressing EWS/ATF1 expression. The RNA-seq analysis was performed by the following method. The total RNA was extracted from each cell by using RNeasy Plus Mini Kit (Qiagen, Hilden, Germany), and the library was produced using TruSeq Stranded Total RNA with Ribo-Zero Gold LT sample Prep kit (illumina). Using KAPA Library Quantification kits (NIPPON Genetics), the concentration was quantified, and sequencing was performed by Hiseq2500 (illumina) and using Hiseq PE Rapid Cluster kit v2-HS. The sequence data was analyzed using TopHat software and Cufflinks software, and visualized by IGV (Integrative Genomics Viewer).

Example 8

Production of Reporter Cell

Figure 7:
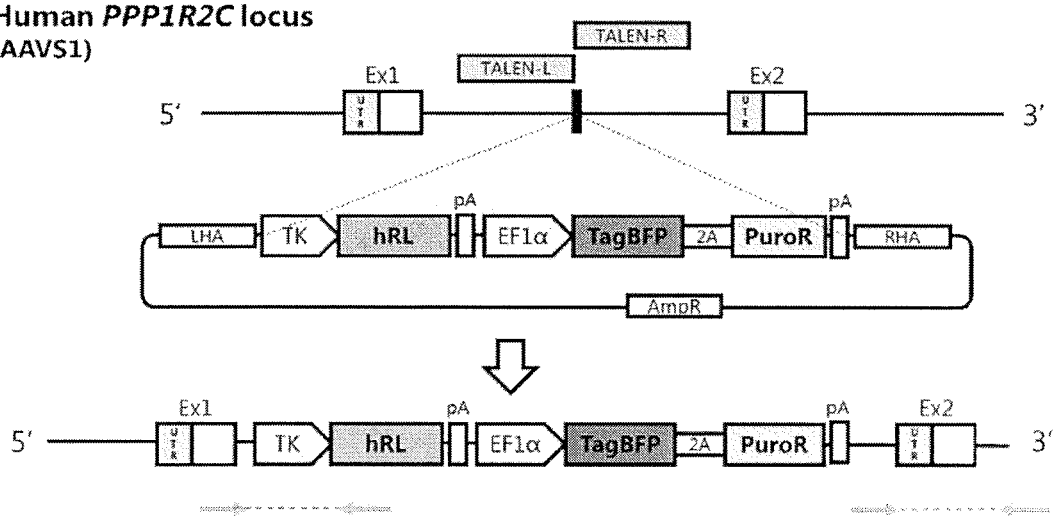
FIG. 7A is a schematic drawing describing a construct of a targeting vector for producing a reporter cell, and a method of introducing the construct into a PPP1R2C gene locus of HEK293 cells derived from human fetal kidney by a genome editing technique using TALEN. In the Figure, hRL shows synthetic Renilla luciferase gene, TagBFP shows blue fluorescence protein gene, and PuroR shows puromycin resistance gene. In addition, LHA and RHA show homology arm on the left side and the right side, respectively.
FIG. 7B shows an outline of luciferase assay performed using the construct of FIG. 7A (left Figure) and the results thereof (right Figure). The horizontal axis of the graph shows the number of cells, and the vertical axis shows relative luminescence intensity of luciferase.
Figure 7:
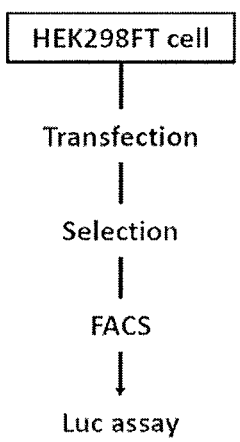
Figure 7:
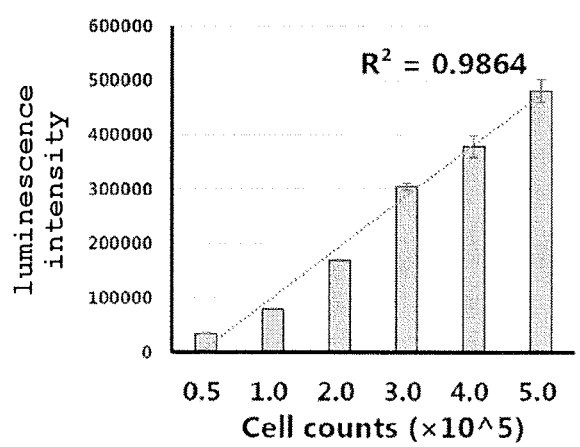

As shown in FIG. 7A, reporter cells stably expressing TagBFP and synthetic Renilla luciferase (hRL) were produced by a genome editing technique using TALEN, and using a targeting vector containing TagBFP gene, synthetic Renilla luciferase (hRL) gene and puromycin resistance gene as reporter genes, and knocking in the reporter gene between exon1 and exon2 in the PPP1R2C gene locus of the HEK298 cell. TagBFP expressing cells were selected by cell sorting using FACS, and luciferase assay was performed. For the luciferase assay, Dual-Luciferase Reporter Assay System (Promega) was used, and the cells were dissolved in Passive lysis buffer, and measured by Envison 2104 Multi-label Reader (PerkinElmer). The results are shown in FIG. 7B. A high positive correlation was found between the cell number and the luminescence intensity ($R^2=0.9864$).

A reporter gene can be introduced into cancer cell by a similar method, and the number of the thus-produced reporter cells can be calculated by the intensity of luciferase luminescence.

Figure 8:
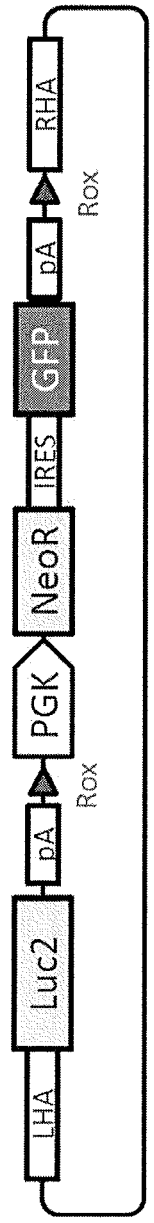
FIG. 8 is a schematic drawing describing a construct of a targeting vector for producing a reporter cell, and a method of introducing the construct into a Nanog gene locus of mouse cancer cell by a genome editing technique using CRISPR/Cas9. In the Figure, Luc2 shows fireflyluciferase gene, GFP shows green fluorescence protein gene, and NeoR shows neomycin resistance gene. Rox shows target sequence of site-specific recombinant enzyme Dre, and sgRNA shows single strand guide RNA.
Figure 8:
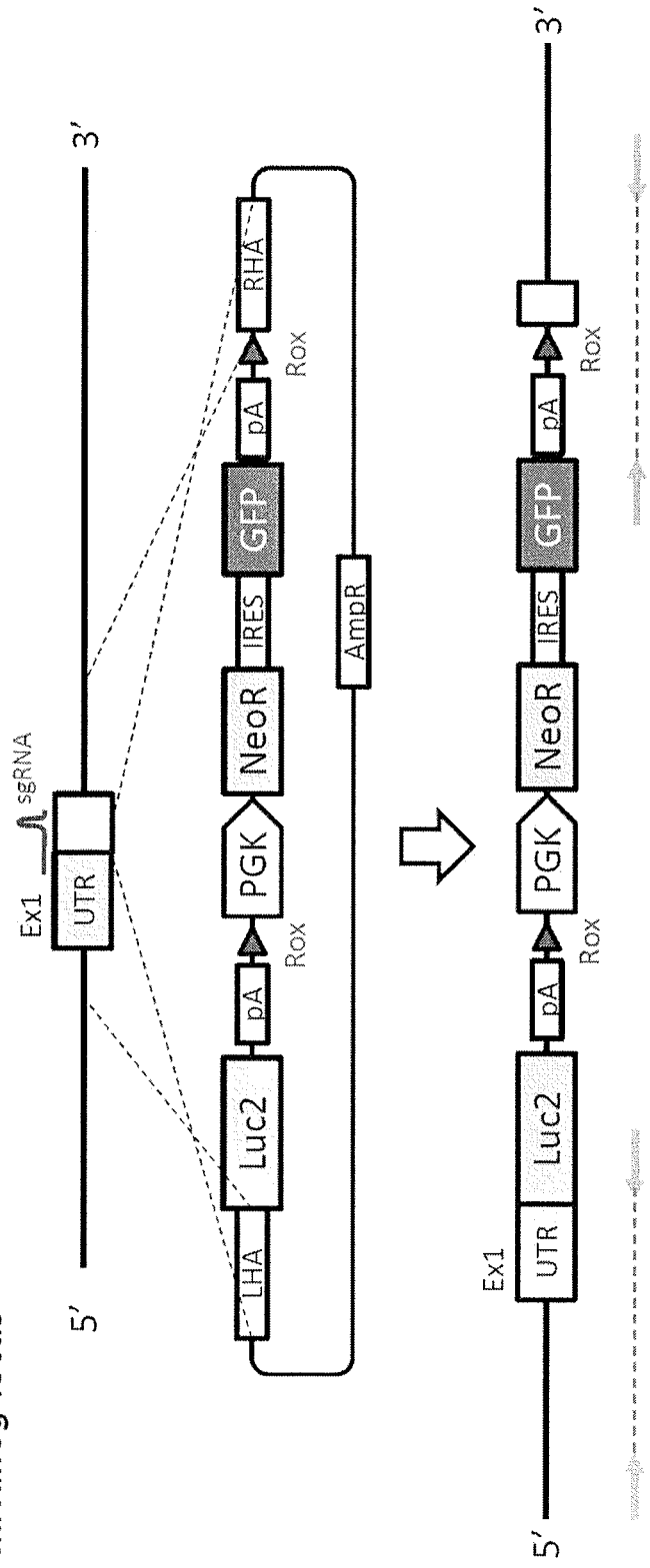

As shown in FIG. 8, a targeting vector containing GFP gene, modified fireflyluciferase (Luc2) gene and neomycin resistance gene as reporter genes was produced. By a genome editing technique using CRISPR/Cas9, and using the targeting vector, the reporter gene can be knocked in between 5' untranslated region (5'UTR) and coding region (CDS) of exon1 in the Nanog gene locus of the mouse cancer cell.

Figure 9:
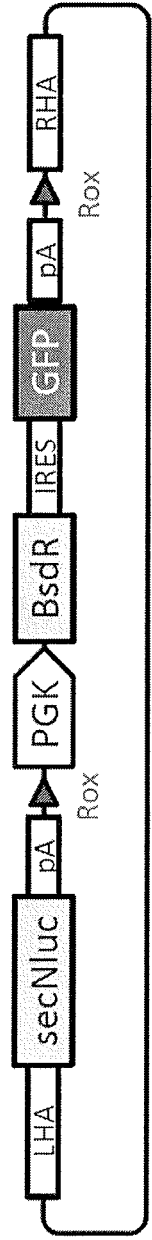
FIG. 9 is a schematic drawing describing a construct of a targeting vector for producing a reporter cell, and a method of introducing the construct into a Nanog gene locus of mouse cancer cell by a genome editing technique using CRISPR/Cas9. In the Figure, secNluc shows secretory NanoLuc™ luciferase gene, and BsdR shows Blasticidin resistance gene.
Figure 9:
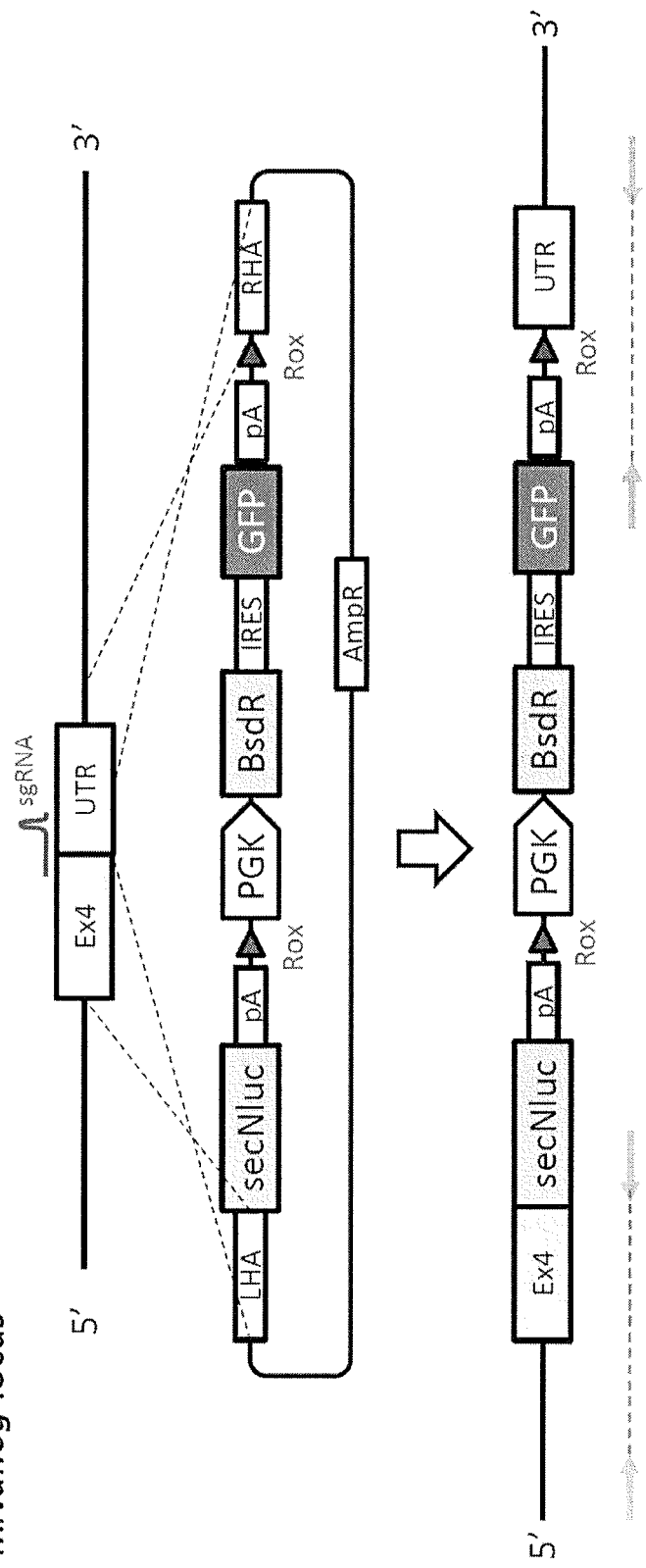

As shown in FIG. 9, a targeting vector containing GFP gene, secretory NanoLuc™ luciferase (secNluc) gene and Blasticidin resistance gene as reporter genes was produced. By a genome editing technique using CRISPR/Cas9, and using the targeting vector, the reporter gene can be knocked in between CDS and 3' untranslated region (3'UTR) and coding region (CDS) of exon4 in the Nanog gene locus of the mouse cancer cell.

Figure 10:
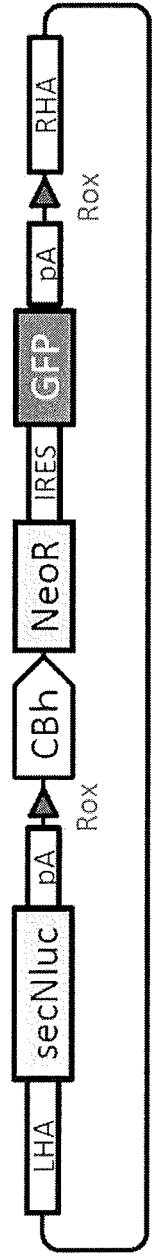
FIG. 10 is a schematic drawing describing a construct of a targeting vector for producing a reporter cell, and a method of introducing the construct into a Nanog gene locus of human cancer cell by a genome editing technique using CRISPR/Cas9.
Figure 10:
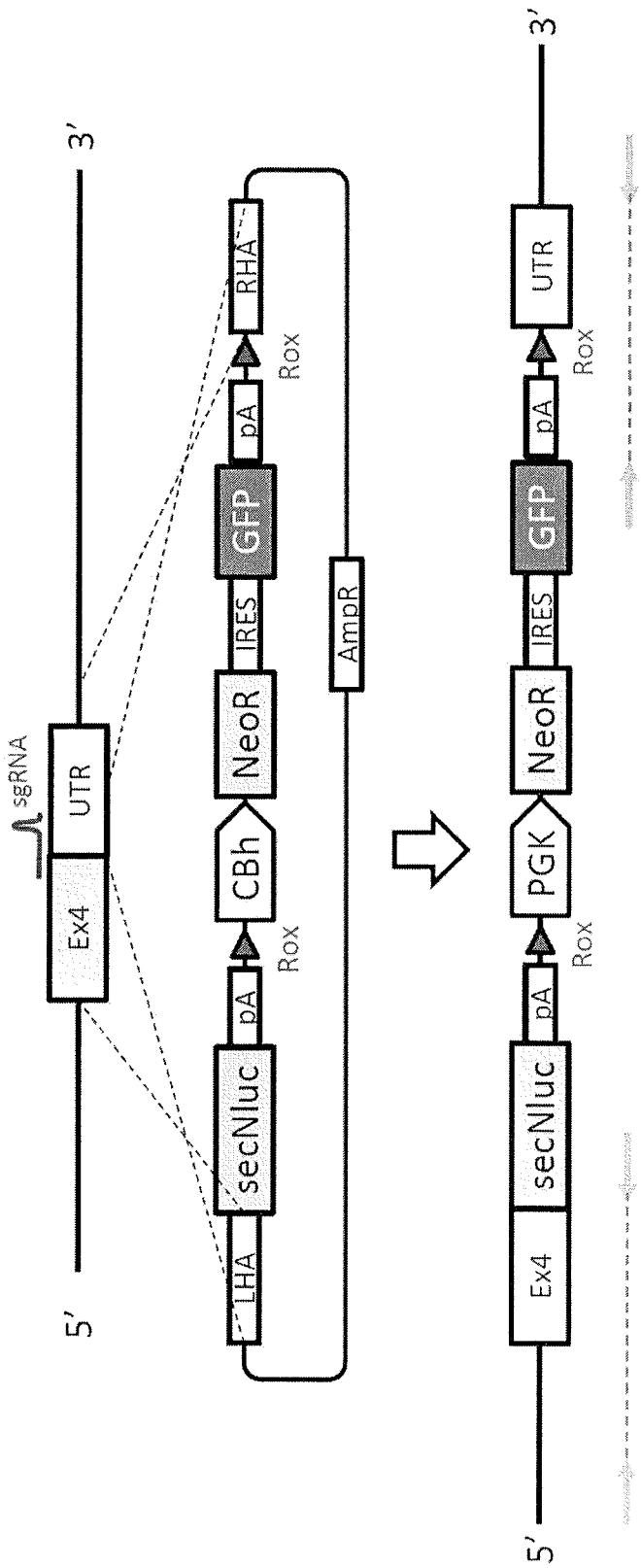

As shown in FIG. 10, a targeting vector containing GFP gene, secretory NanoLuc™ luciferase (secNluc) gene and neomycin resistance gene as reporter genes was produced. By a genome editing technique using CRISPR/Cas9, and using the targeting vector, the reporter gene can be knocked in between CDS and 3' untranslated region (3'UTR) and coding region (CDS) of exon4 in the Nanog gene locus of the human cancer cell.

Since the thus-produced cells express a reporter gene simultaneously with the expression of Nanog, reprogramming of cancer cell can be evaluated using the cells, even without measuring the expression level of undifferentiation-specific genes such as Nanog and the like, and the cells are suitable for application of the screening method of the present invention.

As discussed above, it was shown that oncogene signal can maintain characteristics of the cancer cell, namely, inhibits reprogramming of cancer cells. On the other hand, it was also shown that an anticancer agent targeting oncogene promotes early stages of the reprogramming of cancer cells. These results indicate that a drug inhibiting oncogene signal can place cancer cells in a condition tolerant to the change of cell fate. Therefore, the signal of an important oncogene can be detected by examining the influence of a drug inhibiting a particular signal in cancer cells on the reprogramming.

This application is based on a patent application No. 2015-77264 filed in Japan (filing date: Apr. 3, 2015), the contents of which are incorporated in full herein.

The invention claimed is:

1. A method of screening for a therapeutic drug for cancer, comprising the following steps:
   (i) a step of expressing reprogramming factors in a target cancer cell under contact or no contact with a test substance,
   (ii) a step of confirming change in the cancer cell, and
   (iii) a step of selecting the test substance as a candidate for a therapeutic drug for cancer when the change of cancer cell increased under contact with the test substance as compared to no contact therewith,
   wherein the reprogramming factors comprise Oct3/4, Sox2, Klf4, and c-Myc,
   wherein the change in the cancer cell is change into a more undifferentiated state,
   wherein the change into a more undifferentiated state is evaluated using the number of cells positive for an undifferentiation-specific antigen, or an expression level of an undifferentiation-specific gene in the cancer cell as an index,
   wherein the undifferentiation-specific gene is one or more genes selected from Nanog, Epcam, Cdh1, Fbxo15, PODXL, and GDF3, and
   wherein the cancer has a gene related to intracellular signals involved in proliferation or progression of the cancer.

* * * * *